United States Patent
Benjamin, Jr. et al.

(10) Patent No.: US 9,265,753 B2
(45) Date of Patent: Feb. 23, 2016

(54) LIMITED RELEASE LINGUAL THIOCTIC ACID DELIVERY SYSTEMS

(76) Inventors: Jeffery Lee Benjamin, Jr., Mesa, AZ (US); William Carlton Zolentroff, New York, NY (US)

( * ) Notice: Subject to any disclaimer, the term of this patent is extended or adjusted under 35 U.S.C. 154(b) by 0 days.

(21) Appl. No.: 13/602,093

(22) Filed: Aug. 31, 2012

(65) Prior Publication Data

US 2013/0136703 A1    May 30, 2013

Related U.S. Application Data

(60) Provisional application No. 61/575,900, filed on Aug. 31, 2011.

(51) Int. Cl.
| | | |
|---|---|---|
| *A61K 9/22* | (2006.01) | |
| *A61K 31/34* | (2006.01) | |
| *A61K 31/385* | (2006.01) | |
| *A61K 45/00* | (2006.01) | |
| *A61K 9/00* | (2006.01) | |
| *A61K 9/20* | (2006.01) | |
| *A61K 45/06* | (2006.01) | |

(52) U.S. Cl.
CPC ............ *A61K 31/385* (2013.01); *A61K 9/0056* (2013.01); *A61K 9/2018* (2013.01); *A61K 45/00* (2013.01); *A61K 45/06* (2013.01)

(58) Field of Classification Search
USPC ........................................... 514/440; 424/468
See application file for complete search history.

(56) References Cited

U.S. PATENT DOCUMENTS

| | | |
|---|---|---|
| 6,271,254 B1 | 8/2001 | Ulrich |
| 7,858,655 B2 | 12/2010 | Rohnert |
| 2007/0190114 A1 * | 8/2007 | Smart ........................... 424/440 |
| 2007/0196442 A1 * | 8/2007 | Heuer ........................... 424/439 |
| 2008/0095741 A1 * | 4/2008 | Wessel et al. ................ 424/85.4 |
| 2009/0104171 A1 | 4/2009 | Pardee |

FOREIGN PATENT DOCUMENTS

| | | |
|---|---|---|
| CA | 2135535 | 5/1995 |
| DE | 20207569 U1 | 5/2002 |
| EP | 0654484 A2 | 5/1995 |
| JP | 2006219467 A | 8/2006 |
| KR | 20070110729 | 11/2007 |

OTHER PUBLICATIONS

Mijnhout, Alpha lipoic acid for symptomatic peripheral neuropathy in patients with diabetes: a meta-analysis of randomized controlled trials, International Journal of Endocrinology, Published online Jan. 26, 2012, pp. 1-8, article ID:456279, Hindawi Publishing Corp., Cairo Egypt (Published online).

Ziegler, Treatment of Symptomatic Diabetic Polyneuropathy With the Antioxidant a-Lipoic Acid, Diabetes Care, Aug. 1999, 1296-1301, vol. 22, No. 8, Indianapolis, USA (Published online).

Kallai, Evaluation of drug release from coated pellets based on isomalt, sugar, and microcrystalline cellulose inert cores, AAPS PharmSciTech, Mar. 2010, vol. 11(No. 1), p. 383-391, (Published online).

* cited by examiner

*Primary Examiner* — Adam C Milligan

(57) ABSTRACT

A diffusion rate limiting matrix is utilized to lingually and/or sublingually deliver thioctic acid. This limited release matrix is intended for general nutritional supplementation and/or the treatment of various physiological disorders. Due to its lingual nature, this rate limiting matrix can produce IV-equivalent plasma levels and is not meant to be swallowed.

20 Claims, No Drawings

LIMITED RELEASE LINGUAL THIOCTIC ACID DELIVERY SYSTEMS

CROSS-REFERENCE TO RELATED APPLICATIONS

This application claims the benefit of U.S. provisional patent application No. 61/575,900 (confirmation number 9826), filed on Aug. 31, 2011.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

1. Field of the Invention

The present invention relates to limited release lingual/sublingual delivery systems for thioctic acid.

Thioctic acid is also known as lipoic acid, alpha lipoic acid, or ALA. Thioctic acid has two chiral enantiomers, R-(+)-lipoic acid (RLA) and S-(−)-lipoic acid (SLA), and a racemic mixture of the two R/S-Lipoic acids also exists. Additionally, each of these thioctic acid enantiomers exist in reduced (dihydro-lipoic acid) and oxidized forms. The limited release lingual/sublingual delivery system of this disclosure is effective for any and all of the above thioctic acid variants. The term thioctic acid refers to all of these various species of lipoic acid, unless specifically referred to otherwise.

2. Description of the Related Art

Thioctic acid is believed to be beneficial in several applications, such as preventing organ dysfunction, the treatment of various neuropathies and polyneuropathies, and use as an antioxidant. Thioctic acid has been primarily administered by two methods in the prior art.

First, it has been administered via intravenous (IV) therapy. In IV therapy, a solution containing thioctic acid is delivered through an IV needle directly to a patient's blood stream. This method shows the benefits of a high absorption rate and high plasma levels.

IV therapy becomes problematic, however, when the therapy is designed for use in the long-term care of a patient. In order to utilize IV therapy as a delivery system, the IV must be administered by a medical professional. This typically requires the patient to visit a healthcare provider's office or hospital each time the thioctic acid is to be administered. The time required to visit the office frequently discourages the patient from continuing these visits. Thus, the patient will often discontinue treatment due to the inconvenience of making trips to the provider's office. The necessity for treatment through an office or hospital also creates a high cost for patients, insurance companies, and researchers who want to perform clinical trails. Furthermore, in the event that the patient continues treatment, frequent IV use may cause vein collapse and oxidative stress in the patient.

The second method typically utilizes an orally administered, GI delivery system using a tablet, powder, or soft-gel formulation of thioctic acid. This offers a method of administration which does not require a health care provider's oversight. However, tablets and powders of thioctic acid are difficult for the human body to absorb.

Refined thioctic acid is insoluble in water at normal pH and at the acid pH seen in the stomach, although it is soluble in fat solvents. The dl-form of thioctic acid is likewise insoluble in water and soluble in fat solvents, but it can form a water-soluble sodium salt that is aqueous in water solutions that exist at a pH of about 7.4. However, this sodium salt also has a poor solubility at acid pH.

Due to this solubilization problem, thioctic acid taken in tablet and powder forms is almost entirely dependent upon bile salts in the small intestine for dispersal, which results in a slow absorption rate and low systemic plasma levels. Once bile salt dispersal of thioctic acid crystals has occurred, thioctic acid can penetrate epithelium in the manner of fat-soluble drugs, as well as utilize absorption mechanisms in the small intestine specific to medium chain fatty acids. Soft-gel variations of solubilized thioctic acid, and oral solutions, have been developed to speed up the dispersal process. However, for the most part these solutions are prone to polymerization and degradation reactions and are unstable during long term storage. More significantly, all previous oral delivery systems (including soft-gels and oral solutions) utilize the stomach and gastrointestinal (GI) tract for absorption.

Since the liver is the major organ implicated in the removal of thioctic acid from plasma, with a removal rate nearly equal to that of the clearance of plasma through the liver, slow GI absorption rates result in low systemic plasma levels due to the necessary passage of ingested substances through the hepatic portal vein of the liver (the first pass mechanism).

Due to the insoluble nature of thioctic acid and/or the liver's function to remove it from both systemically circulating plasma and the first pass mechanism of the hepatic portal vein, oral delivery systems that utilize the stomach and small intestine for absorption necessarily equate to relatively low absorption profiles, such that only a small percent of a given dose actually becomes utilized by the body. Therefore, a large degree of waste occurs when GI absorption mechanisms are utilized, and thus maximal benefits from thioctic acid supplementation are not achieved through GI absorption mechanisms.

Previous attempts to overcome the low absorption profiles of oral thioctic acid doses have produced their own problems and side-effects. When high concentrations of thioctic acid make continued contact with cells in the mouth and GI tract (including the stomach), those cells may swell and burst, causing an apoptotic "burn" effect. This apoptotic effect is what caused lethality in animals utilized for LD50 studies, where said animals died from liver failure. Upon histological examination, liver mitochondria of said animals were seen to have burst due to an osmotic imbalance as thioctic acid flooded into these cells. As such, due to this osmotic/apoptotic effect current formulations of a swallowed tablet, powder, or soft-gel can be uncomfortable or harmful to the patient, particularly when taken in high enough doses to produce IV equivalent plasma levels.

A solution is needed to address one or more of these shortcomings in the prior art.

BRIEF SUMMARY OF THE INVENTION

A limited release lingual/sublingual delivery system for thioctic acid is provided.

A diffusion limiting binding agent, either hard or soft, in the lingual/sublingual formulations may include, but are not limited to: sucrose, isomalt, dextrose, lactitol, sorbitol, maltose and chicle.

The limited release lingual/sublingual delivery system may be a lozenge, caramel, gum, or other release limiting matrix formulation placed in the patient's mouth that that is intended to remain in the mouth. That is, the patient is not encouraged to swallow the delivery system. The formulation contains a concentration of thioctic acid between 1% and 25% by mass, preferably at a concentration of approximately 2% by mass.

Individual lozenges, candies, or other lingual delivery systems are expected to be from 1.0 g to 30.0 g, with thioctic acid dose variations between 10 mg to 600 mg. However, extremely low dose variations (from 5.0 mg to 10 mg) of thioctic acid are anticipated, such that lozenges for general consumption as a supplement are also included, in addition to the high dose formulations intended for specific therapeutic effects. These therapeutic applications may include the treatment of Alzheimer's, Diabetic peripheral neuropathies, retinal neuropathies, and other physiological states where thioctic acid therapy is advised or under investigation.

BRIEF DESCRIPTION OF THE SEVERAL VIEWS OF THE DRAWING

Not Applicable.

DETAILED DESCRIPTION OF THE INVENTION

Through the course of study, while inventing the first marketed form of solubilized thioctic acid (ThioGel™), the inventor of this limited release lingual/sublingual delivery system noted that solubilized forms of thioctic acid, be they in aqueous solutions or in fat solvents, are able to pass through the epithelium of the mouth and GI tract due to the dispersed nature of the molecules. However, initial attempts to utilize lingual absorption mechanisms resulted in a burn effect that was revealed to be the apoptotic effect observed in the livers of animals utilized for LD50 studies.

The present limited release invention addresses these negative effects through the use of sucrose-based and non-sucrose based candies, gums, and lozenges in various concentration and flavor combinations. A flavored lingual/sublingual delivery system in the concentration range of 1%-6% thioctic acid (by mass), not only removes and/or minimizes these effects, it also improves the palatability of the raw compound (thioctic acid).

Provided that the lingual/sublingual delivery system is homogeneous, and the thioctic acid concentration is within the preferred range, the release of thioctic acid onto lingual surfaces is delayed and dispersed enough that the burn effect is overcome, especially within the concentration range of 1-3% thioctic acid (by mass). This means an 11-gram lozenge, candy, gum, or other lingual delivery system can be utilized to deliver 200 mg of thioctic acid without noticeable negative effects. Slightly greater concentrations (up to the 6% range) can also be utilized without excessive negative effects, but as the concentration increases so too does the burn effect.

This limited release lingual/sublingual delivery system is unique for the following reasons.

First, in other lingual/sublingual delivery systems the relative concentration of the active substance poses no immediate danger or discomfort. Therefore, high doses may be given without any ill effects. In contrast, thioctic acid can not be placed in the mouth at high concentrations without the apoptotic burn. Thus, it is imperative that the suspension matrix release a limited amount of thioctic acid into the mouth at any given moment. Liquid drops and/or compression tablets which are intended to remain in the mouth, may place too high a concentration in local areas of the mouth at any given moment. The compression tablets, the typical method used for sublingual delivery, dissolve slowly for a sustained period of time, but then disintegrate and release a higher dose of active ingredient at the end of the delivery. The spike in active ingredient delivery is not a problem for the general sustained release of many vitamins and supplements, but is possibly problematic for thioctic acid. Accordingly, this invention can use a sustained release mechanism but preferably provides a limited release mechanism. Both mechanisms provide a slow release of the active ingredient for a significant duration of time, but the limited release mechanism never increases the rate of active ingredient release. Note that buccal patches are unsuitable, because they are designed for rapid release of the active ingredient, which could possibly lead to sores as an apoptotic burn may occur on the inner cheek due to the limited exposure area.

Secondly, thioctic acid is co-transported into cells along with glucose. This means that mechanisms for thioctic acid absorption exist in the buccal cavity, where sugar is readily absorbed. Therefore, unlike many lingual/sublingual vitamins and supplements, faster and more complete absorption of thioctic acid can occur in the mouth, because of the co-presence of sugar in the saliva. Many lingual/sublingual delivery systems are not very effective. The act of swallowing leads to GI absorption as the primary route of absorption.

Perhaps most importantly, data on the pharmacokinetics of thioctic acid in diabetes and other pathological states implies that peak plasma levels and percent utilization (based upon an area under the curve analysis) are more important than specific oral doses. Based upon this assumption, and data that shows superior peak plasma levels for limited release lingual versus GI absorption delivery systems, limited release lingual delivery systems are expected to be more effective than GI delivery systems, such that less thioctic acid is needed to achieve the same effects. Thus, IV-like beneficial effects using this limited release lingual delivery system are actually expected to exist at a range of 300-600 mg thioctic acid, which equates to a lozenge-like formulation with a total mass of only 18-36 g. It is impossible to achieve the same IV equivalent plasma levels in GI delivery systems without associated deleterious side effects with such high doses.

Finally, the key to the creation of the initial limited release lingual formulation lies in the melting points of sugar and isomalt relative to the sublimation temperature of thioctic acid. Since thioctic acid sublimates (ie, goes from a solid to a gaseous phase without turning into a liquid or breaking down) above 160 degrees Celsius, and sucrose and isomalt formulations are commonly made below this sublimation temperature, it is possible to add thioctic acid to molten sucrose or isomalt without changing the structure of the thioctic acid itself. Thus, a wide range of sugar and sugar substitute based formulations are possible. During this process, thioctic acid can be combined with the molten release limiting matrix both prior to the addition of secondary flavoring compounds and after flavoring oils are added. For most other vitamins and drugs this temperature range would pose a problem.

One of the side effects observed during IV delivery of thioctic acid is a hypoglycemic response. For this reason, even for diabetics, glucose is commonly added to the IV mixture. This hypoglycemic response has never been reported for existing oral delivery systems. However, during initial testing of the limited release lingual delivery system a significant number of test subjects experienced this hypoglycemic response. Therefore, not only are IV plasma levels obtained by the limited release lingual delivery system, but associated side effects as well. This implies the same therapeutic effects obtained during IV delivery can be expected during clinical trials.

However, many diabetic patients placed under thioctic acid therapy might be uncomfortable with a sucrose-based delivery system. Therefore, a sugar-free version of the lingual delivery system was created, in which isomalt was used in the place of sucrose. This isomalt variation shows the same basic characteristics as the sucrose formulation originally tested.

In both the sucrose and sugar-free formulations tested, the release of thioctic acid from the dispersal medium occurs slowly, as the lingual delivery formulation dissolves. Thus, thioctic acid is spread across lingual surfaces in local concentrations that remain low at any given moment. This means that the cellular burn described above is minimized, and thioctic acid can be quickly delivered to systemic circulation in doses that reach high plasma concentrations (especially in comparison to GI absorption levels) without flooding local cells.

The rate at which the limited release lingual/sublingual delivery system dissolves in the mouth is not a simple matter of dissolving the matrix in water. The mouth contains specific enzymes that are designed to break down complex sugars, as well as mechanisms for the absorption of simple sugars. Accordingly, including substances that inhibit enzymatic breakdown of the matrix will slow the rate of dissolution and thus affect the relative concentration in the mouth. An obvious example is the isomalt matrix itself, which contains a synthetic sugar related to sucrose which can not be cleaved into glucose and fructose due to the inverted nature of its covalent bond. This matrix dissolves slower in the mouth than the sucrose based matrix. Thus, the isomalt matrix itself is a slight inhibitor of thioctic acid release.

To any of the above mentioned formulations, the addition of specific compounds that inhibit the rate of breakdown is intended. Because there are no specific enzymes in the mouth responsible for breaking down proteins and lipid-like substances, these ingredients will further limit the release of thioctic acid into the mouth, overcoming the apoptotic burn, while enabling lingual absorption mechanisms to bypass the first pass mechanism of the liver. A few specific examples include lecithin, glycine, potassium bitartrate (cream of tarter), protein hydrolysate, hydrolyzed collagen, linolenic acid, and/or other food grade proteins and fatty acids.

Preliminary data obtained during formulation testing (see below for manufacturing details) shows that a 2% thioctic acid concentration formulation of 600 mg reaches a peak plasma level of 2,070 ng 15 minutes after the isomalt lozenge is placed into the mouth. In comparison, an equivalent dose of an orally administered tablet reaches a peak level of 840 ng in 60 minutes. Of particular note is the fact that IV doses within the same dose range, tested by the same methods, reached peak plasma levels of 1,900 ng, since high IV plasma levels are required for maximum benefit. Given this information, and the high peak levels lingual formulations are able to achieve, lingual dosing is it likely to prove therapeutically equivalent to IV dosing and negate the need for invasive needles and expensive medical monitoring when a patient is entered into thioctic acid treatment regimes.

The present invention includes the use of lingual and sublingual delivery systems for thioctic acid, wherein the delivery system is either sucrose or non-sucrose based. The limited release lingual/sublingual delivery system may be a lozenge, gum, or other release limiting matrix formulation placed in the patient's mouth and intended to remain in the mouth. The formulation contains a concentration of thioctic acid between 1% and 25% by mass, preferably at a concentration of approximately 2% by mass.

A diffusion limiting binding agent, either hard or soft, in the lingual/sublingual formulations may include, but are not limited to: sucrose, isomalt, dextrose, lactitol, sorbitol, maltose and chicle.

Inactive ingredient variations in the lingual/sublingual formulations may include, but are not limited to: hydrogenated starch, hydrolysate, gluconic acid, malic acid, lactic acid, sodium lactate, aspartame, glycine, corn syrup, lecithin, cream of tarter, honey, fruit juices, vegetable juices, water, and flavoring oils or alcohols.

Active ingredients in addition to thioctic acid may include (but are not limited to): Selenium, Vitamin E, Vitamin C, Chromium, Potassium, Calcium, gamma-linolenic acid, myoinositol, Vitamin B, Coenzyme Q and various herbal extracts, including, but not limited to, cinnamon, chamomile, althea, anise, eucalyptus, peppermint, elder, fennel, licorice, rose hips, sage, and thyme.

Individual lozenges, candies, or other lingual delivery systems are expected to be from 1.0 g to 30.0 g, with thioctic acid dose variations between 10 mg to 600 mg. However, extremely low dose variations (from 5.0 mg to 10 mg) of thioctic acid are anticipated, such that lozenges for general consumption as a supplement are also included, in addition to the high dose formulations intended for specific therapeutic effects. These therapeutic applications may include the treatment of Alzheimer's, Diabetic peripheral neuropathies, retinal neuropathies, and other physiological states where thioctic acid therapy is advised or under investigation.

Concentrations below 1% are possible and acceptable in terms of this preventing thioctic acid burn. However, the issue of having enough thioctic acid to deliver a meaningful dose becomes an issue. From this it would be reasonable to assume that smaller doses, such as 30 mg per day, would still provide some beneficial effects. 30 mg per day spread out over six doses (one before and after each meal) would result in an individual dose of 5 mg. Accordingly, even doses as small as 5 mg, to be taken multiple times during the course of the day may provide an effective dose to act as a meaningful maintenance level or prophylactic level of thioctic acid supplementation.

For therapeutic or supplementation purposes in which RLA is believed to be exclusively or primarily effective, the dose might theoretically be cut by 50% for the same effective dose as racemic ALA (or possibly by 25% if SLA interferes with RLA utilization). Accordingly, the low end of the concentration range discussed in this patent should be read to represent values that are multiplied by a factor of 50% (or possibly 25%) when using the possibly more effective thioctic acid enantiomer. The same is true for minimum milligrams of dosing. For example, the 5 mg minimum listed for thiotic acid would be reduced to 2.5 mg (or possibly 1.25 mg). Thus, in cases where the theoretically more active enantiomer is utilized the minimum concentration range of 1% thioctic acid would actually reflect a minimum concentration range of 0.5% (or 0.25%) when that enantiomer is used alone in the limited release lingual system.

Sucrose Based Lingual Thioctic Acid Manufacturing Process (Small Scale)

Prior to adding the raw thioctic acid, insure it is finely powderized with a mortar and pestle. This will make it easier to insure a homogeneous mixture is obtained.

In a stainless steel saucepan add 1.0 cup of sugar (185 g), ½ cup light corn syrup (148 g), and ¼ cup of water (64 g). Using a candy thermometer, heat the mixture up to 300 degrees Fahrenheit, stirring occasionally with a stainless steel spoon.

As soon as correct temperature is reached add ¼ teaspoon (1.3 g) red food coloring, and ½ teaspoon (2.7 g) of cinnamon oil. Mix in completely (avoid stirring too much or candy will become a sugary lump).

Remove from heat and add 10 g of Thioctic acid. Quickly mix in completely, insuring that mixture becomes homogeneous (lumps or specks will result in a matrix that has a high concentration in small pockets, which can cause problems during administration). - - - Perform this step in a well ventilated area, since a small fraction of the thioctic acid will sublimate.

Immediately pour into hard candy molds that have been lightly coated with vegetable oil (this makes it easier to remove the candy once it has cooled). Let cool completely.

Dust with powdered sugar. This minimizes water absorption during storage and keeps the pieces from sticking together. Store at room temperature away from direct sunlight in sealed baggies or Tupperware containers. For clinical studies, place each lozenge in its own blister pack compartment.

The above recipe yields a 2.5% thioctic acid limited release lingual lozenge. Exact dosage will depend upon the size of the molds utilized.

Isomalt Based Lingual Thioctic Acid Manufacturing Process (Small Scale)

Prior to adding the raw thioctic acid, insure it is finely powderized with a mortar and pestle. This will make it easier to insure a homogeneous mixture is obtained.

In a stainless steel saucepan add 1.0 cup of Isomalt (185 g), and 4 tablespoons of water (60 g). Using a candy thermometer, heat the mixture up to 300 degrees Fahrenheit, stirring occasionally.

As soon as correct temperature is reached add ¼ teaspoon (1.3 g) red food coloring, and ½ teaspoon (2.7 g) of cinnamon oil. Mix in completely (avoid stirring too much or candy will become a sugary lump).

Remove from heat and add 6.5 g of Thioctic acid. Quickly mix in completely, insuring that mixture becomes homogeneous (lumps or specks will result in a matrix that has a high concentration in small pockets, which can cause problems during administration). - - - Perform this step in a well ventilated area, since a small fraction of the thioctic acid will sublimate.

Immediately pour into hard candy molds that have been lightly coated with vegetable oil (this makes it easier to remove the candy once it has cooled). Let cool completely.

Store at room temperature away from direct sunlight in sealed baggies, Tupperware containers, or individual blister packs.

The above recipe yields a 2.6% thioctic acid limited release sugar-free lozenge.

CONCLUSION

When the diffusion limiting binding agent is used as a lingual/sublingual delivery system, it provides a uniquely and synergistically effective method of delivering thioctic acid to a patient's bloodstream in supplemental and therapeutic doses.

We claim:

1. A method of minimizing the burning sensation associated with oral mucosal administration of alpha lipoic acid (ALA), comprising:
    providing a hard candy lozenge comprising a therapeutically effective amount of ALA dispersed in a release limiting matrix,
    administering the lozenge comprising placing the lozenge into the oral cavity of an individual and permitting the lozenge to remain intact in the oral cavity for a sufficient period of time for the lozenge to dissolve completely,
    wherein the lozenge has an ALA release rate which is less than the release rate of a small scale lozenge weighing 3 grams and made by (1) heating a matrix consisting of 185 grams of sugar, 148 grams of light corn syrup, 64 grams of water, 1.3 grams of red food coloring, 2.7 grams of cinnamon oil and 6% by mass ALA to 300° F., (2) pouring the matrix into a hard candy mold and (3) cooling completely.

2. The method of claim 1, wherein the method produces a peak plasma level more quantitatively similar to the peak plasma level produced through IV administration of an ALA dose within the same dosage range than to the peak plasma level produced by a swallowed tablet containing an ALA dose within the same dosage range.

3. The method of claim 1, wherein the hard candy lozenge comprises at least one of sucrose, glucose and fructose.

4. The method of claim 1, wherein the hard candy lozenge comprises at least one of sucrose and fructose.

5. The method of claim 1, wherein the method provides treatment for retinal neuropathy.

6. The method of claim 1, wherein the method provides treatment for diabetes.

7. The method of claim 1, wherein the method provides treatment for diabetic neuropathy.

8. A method of minimizing the burning sensation associated with oral mucosal administration of ALA, comprising:
    (A) providing a hard candy lozenge comprising a prophylactically effective amount of ALA dispersed in a release limiting matrix;
    (B) administering the lozenge comprising placing the lozenge into the oral cavity of an individual and permitting the lozenge to remain intact in the oral cavity for a sufficient period of time for the lozenge to dissolve completely; and
    C) wherein the lozenge has an ALA release rate which is less than the release rate of a small scale manufactured lozenge weighing 3 grams and made by (1) heating a matrix consisting of 185 grams of sugar, 148 grams of light corn syrup, 64 grams of water, 1.3 grams of red food coloring, 2.7 grams of cinnamon oil and 6% by mass ALA to 300° F., (2) pouring the matrix into a hard candy mold and (3) cooling completely.

9. The method of claim 8, wherein the method produces a peak plasma level more quantitatively similar to the peak plasma level produced through IV administration of an ALA dose within the same dosage range than to the peak plasma level produced by a swallowed tablet containing an ALA dose within the same dosage range.

10. The method of claim 8, wherein the hard candy lozenge comprises at least one of sucrose, glucose and fructose.

11. The method of claim 8, wherein the hard candy lozenge comprises at least one of sucrose and fructose.

12. The method of claim 8, wherein the method provides treatment for diabetic neuropathy.

13. The method of claim 8, wherein the method provides treatment for diabetes.

14. A method of minimizing the burning sensation associated with oral mucosal administration of ALA, comprising:
    (i) providing a hard candy lozenge comprising 1% to 6% by mass ALA dispersed in a release limiting matrix;
    (ii) administering the lozenge comprising placing the lozenge into the oral cavity of an individual and permitting the lozenge to remain intact in the oral cavity for a sufficient period of time for the lozenge to dissolve completely; and (iii) wherein the lozenge has an ALA release rate which is less than the release rate of a small scale manufactured lozenge weighing 3 grams and made by (1) heating a matrix consisting of 185 grams of sugar, 148 grams of light corn syrup, 64 grams of water, 1.3 grams of red food coloring, 2.7 grams of cinnamon oil and 6% by mass ALA to 300° F., (2) pouring the matrix into a hard candy mold and (3) cooling completely.

15. The method of claim 14, wherein the hard candy lozenge comprises less than 3% by mass ALA.

16. The method of claim 14, wherein the amount of ALA in the hard candy lozenge is 5 mg to 600 mg.

17. The method of claim 14, wherein the method produces a peak plasma level more quantitatively similar to the peak plasma level produced through IV administration of an ALA dose within the same dosage range than to the peak plasma level produced by a swallowed tablet containing an ALA dose within the same dosage range.

18. The method of claim 14, wherein the amount of ALA in the hard candy lozenge is 10 mg to 600 mg.

19. The method of claim 14, wherein the hard candy lozenge comprises at least one of sucrose, glucose and fructose.

20. The method of claim 14, wherein the hard candy lozenge comprises at least one of sucrose and fructose.

\* \* \* \* \*